United States Patent [19]

Hoffmeister

[11] Patent Number: 4,680,945
[45] Date of Patent: Jul. 21, 1987

[54] COOLING CHAMBER FOR PROCESSING SPECIMENS FOR MICROSCOPIC AND ELECTRON-MICROSCOPIC INVESTIGATIONS

[75] Inventor: Dietrich Hoffmeister, Oberkochen, Fed. Rep. of Germany

[73] Assignee: Carl-Zeiss-Stiftung, Heidenheim, Fed. Rep. of Germany

[21] Appl. No.: 863,194

[22] Filed: May 14, 1986

[30] Foreign Application Priority Data

May 15, 1985 [DE] Fed. Rep. of Germany ....... 3517518

[51] Int. Cl.$^4$ .............................................. F25B 19/00
[52] U.S. Cl. ..................................... 62/514 R; 62/45; 62/78
[58] Field of Search .......................... 62/45, 514 R, 78

[56] References Cited

U.S. PATENT DOCUMENTS

| | | | |
|---|---|---|---|
| 3,080,725 | 3/1963 | Cowley et al. | 62/514 R |
| 3,319,431 | 5/1967 | Clarke et al. | 62/45 |
| 3,410,110 | 11/1968 | Hoyes | 62/514 R |
| 4,302,950 | 12/1981 | Sitte | 62/514 R |
| 4,459,825 | 7/1984 | Crouch | 62/457 |

Primary Examiner—Ronald C. Capossela
Attorney, Agent, or Firm—Walter Ottesen

[57] ABSTRACT

A cooling chamber has an interspace between the structure defining the work chamber and coolant vessel on the one hand, and the outer insulating vessel on the other hand to provide better thermal insulation. The work chamber is disposed above the coolant vessel and has apertures formed in the base wall thereof so that the vaporized coolant flows directly into the work chamber. The consumption of coolant is minimal and the cooling chamber is of simple configuration is that it can be manufactured economically.

10 Claims, 1 Drawing Figure

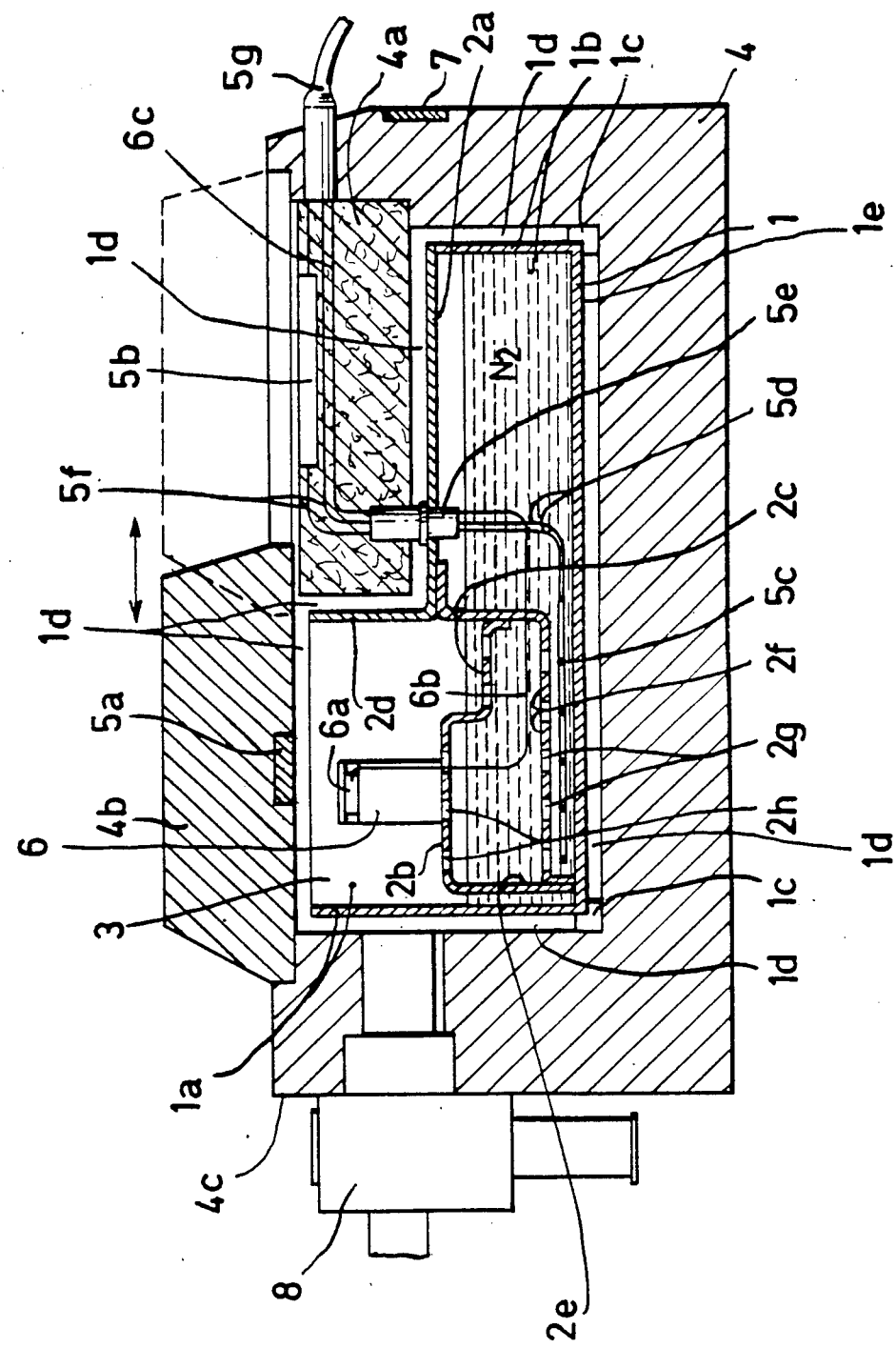

COOLING CHAMBER FOR PROCESSING SPECIMENS FOR MICROSCOPIC AND ELECTRON-MICROSCOPIC INVESTIGATIONS

FIELD OF THE INVENTION

The invention relates to a cooling chamber for processing specimens for microscopic and electron-microscopic investigations. The cooling chamber includes a work chamber, a coolant vessel and an insulating vessel. A portion of the coolant vessel walls serve at the same time as walls of the work chamber, and the work chamber and coolant vessel are surrounded by the insulating vessel. Vaporized coolant is conducted into the work chamber.

BACKGROUND OF THE INVENTION

To an increasing extent, preparation chambers in which both the specimens and the tools are cooled to low temperatures and kept there (so-called cryoprepa-ration) are being used for microscopic and electron-microscopic investigations, particularly of biological specimens. In this connection, neither the specimens nor the tools can be allowed to become frozen over with condensation from the moisture in the air. Liquid nitrogen is used as the coolant in most instances.

Published German patent application DE-OS No. 29 06 153 discloses a cooling chamber in which the work chamber is a block-like vessel made of sheet metal having a good thermal conductivity. This work chamber is provided with feet by which it is secured in a larger coolant vessel, also of block-like configuration, which receives the coolant and, in turn, is mounted in an insulating vessel made of foamed plastic. The insulating vessel is surrounded by a metal housing. The vaporized coolant in the coolant vessel is conducted away through conduits between the insulating vessel and the metal housing. To prevent the outside of the metal vessel from freezing over with moisture from the air, an electric heater must be used to heat this vessel. Condensation of moisture in the air in the work chamber is avoided by flushing the chamber continuously; to this end, helium gas is cooled and dried by means of a cooling coil mounted in the coolant vessel. The helium gas flows out at the bottom of the work chamber and completely fills the work chamber because the work chamber is made to be tight except for its opening at the top.

From published U.S. Pat. No. 4,302,950, it is further known to use part of the vaporized coolant to flush the work chamber. Sheet-metal panels are provided for this purpose on the walls of the work chamber and guide the vaporized coolant to the bottom of the work chamber. U.S. Pat. No. 4,302,950 also discloses an electric heater disposed in the coolant to adjust the quantity of coolant that is vaporized for flushing the work chamber. In this embodiment as well, it is necessary to heat the metal housing to avoid condensation of the moisture in the air.

These known cooling chambers have the disadvantage of requiring relatively large quantities of coolant. In the case of liquid nitrogen, which is used most often, approximately 30 liters are consumed in 5 hours. By present standards, this makes the running costs for routine operation too high.

SUMMARY OF THE INVENTION

It is an object of the invention to provide a cooling chamber in which the consumption of coolant is minimal. Moreover, the cooling chamber is of as simple configuration as possible so that it can be manufactured economically.

This object is attained according to the invention by providing a cooling chamber having an interspace between the insulating vessel and the walls of the coolant vessel and work chamber and, by connecting the walls to the insulating vessel by only a few connecting elements.

In an advantageous embodiment, the work chamber is disposed above the coolant vessel and the bottom of the work chamber has openings through which the vaporized coolant enters the work chamber and fills the same.

In a particularly advantageous embodiment, a displaceable cover is disposed on the top of the work chamber; when the cover is opened, it closes a contact which switches on a heater within the coolant. This heater is dimensioned such that the greater flow of heat entering through the chamber opening is compensated for by the coolant which is additionally vaporized as a consequence of the heating. In this way, the condensing moisture in the air, which forms in the boundary layer between the air and the vaporized coolant at the elevation of the opening, is also swept away completely.

Further advantageous embodiments of the invention will become apparent from the ensuing detailed description.

BRIEF DESCRIPTION OF THE DRAWING

The invention will now be described with reference to the drawing which shows a side elevation view, in section, of an embodiment of a cooling chamber according to the invention.

DESCRIPTION OF THE PREFERRED EMBODIMENTS OF THE INVENTION

In this exemplary embodiment, a block-like coolant vessel 1 is shown which is made for instance of niro-steel. Its side walls 1a shown on the left extend to the upper boundary of the work chamber 3, while the side walls 1b shown on the right extend upwardly only approximately to half that height. This coolant vessel 1 receives the coolant, such as the liquid nitrogen identified as $N_2$ in the drawing, and on its bottom 1e, the vessel is connected with the insulating vessel 4 with as few feet 1c as possible. The feet 1c have a poor thermal conductivity. The insulating vessel 4 may be made of polyurethane foam, for instance, and suitably has a wall thickness of from 4 to 5 cm. There is an interspace 1d approximately 5 mm wide between the coolant vessel 1 and the insulating vessel 4. Together with the insulating vessel 4, this interspace 1d effects such good thermal insulation so that no moisture from the air condenses on the outer wall 4c of the insulating vessel, and the consumption of coolant is approximately 1 liter in 1½ to 4 hours, which is very low.

A part comprising the sections 2a to 2f, which can also be made for example of niro-steel, is set into or onto the coolant vessel 1. The section 2a forms an upper covering over the righthand portion of the coolant vessel 1. Sections 2b and 2c serve as a bottom for the work chamber 3; section 2c enables direct contact with the coolant. Section 2d forms the fourth side wall of the work chamber 3, section 2e acts as a support, and section 2f forms the assembly face for the heating wires 5c. Thus the work chamber 3 is surrounded by four side walls and one bottom face, all of which are in contact with the coolant N₂. The vaporized coolant flows into the work chamber through openings 2h uniformly distributed over the entire bottom and fills it completely (since the coolant is heavier than air). The interspaces 1d are likewise filled with the vaporized coolant.

On the righthand side beside the work chamber 3, above the coolant vessel 1 and its upper covering 2a, the insulating vessel 4 is closed off by the insulating element 4a. The insulating element 4a is disposed at a spacing 1d of approximately 5 mm from sections 2a and 2d as shown. This insulating element 4a is made to be removable, so that the cooling chamber can easily be disassembled. A cover 4b that is displaceable toward the right as shown in phantom outline is disposed above the work chamber 3. The cover 4b is likewise made of polyurethane foam and has a thickness of from 4 to 5 cm. If any manipulation has to be performed in the work chamber 3, the cover 4b is pushed to the right. When this is done, the magnet 5a mounted in the underside of the cover assumes a position above the reed contact 5b in the insulating element 4a. Accordingly, when the cover 4b is opened, the reed contact 5b is closed thereby switching on the heater. This heater comprises wires 5c, which are fastened beneath the section 2f having openings 2g. These wires 5c are connected to an external current source via the lines 5d, a plug 5e, the lines 5f and the reed contact 5b as well as the cable lead-out 5g. When the heater is switched on, coolant is additionally vaporized thereby compensating for the increased inflow of heat through the open cover. Moreover, the condensing air moisture, which forms in the boundary layer between the air and the vaporized coolant at the elevation of the opening, is swept away completely by this additionally vaporized coolant.

A platinum resistance thermometer 6a is located in a portable holder 6 in the work chamber 3. The thermometer connections lead to an external measuring instrument for the temperature in the work chamber 3, via the two-line lead 6b, the plug 5e, the line 6c and the cable lead-out 5g.

A metal band 7, for instance including threaded holes, is attached to the outside of the insulating vessel 4, and any of the usual operating and observation instruments used in cryotechnology that are not inserted directly into the work chamber 3 may be attached to this band 7. Finally, the cooling chamber also has an air lock 8 which is configured in a manner known per se and enables moving the specimen into a transfer container without exposing it to higher temperatures and to the ambient air containing moisture.

It is understood that the foregoing description is that of the preferred embodiments of the invention and that various changes and modifications may be made thereto without departing from the spirit and scope of the invention as defined in the appended claims.

What is claimed is:

1. A cooling chamber for processing a specimen for microscopic and electron-microscopic investigations comprising:
    an insulating vessel having an inner wall surface defining a receiving cavity;
    coolant vessel means for holding a coolant therein disposed in said cavity and having an outer wall surface adjacent said inner wall surface;
    a working chamber for processing the specimen, said working chamber being arranged above said coolant vessel means and having a base defining an apertured interface between the interior of said coolant vessel means and said chamber so as to permit vaporous coolant to pass from said coolant vessel means into said working chamber thereby filling the latter;
    a plurality of spacers arranged at preselected locations between said wall surfaces for supporting said coolant vessel means in spaced relationship to said inner wall surface so as to cause said wall surfaces to conjointly define a space therebetween for thermally insulating said coolant vessel from said insulating vessel; and,
    coolant supply means for supplying vaporized coolant to said work chamber.

2. The cooling chamber of claim 1, comprising displaceable cover means made of heat-insulating material and being displaceable between a first position whereat said work chamber is closed off with respect to the ambient and a second position whereat said work chamber is open and accessible from the ambient.

3. The cooling chamber of claim 1, comprising lock means mounted in a side wall of said insulating vessel for facilitating the placement of a specimen in said work chamber.

4. The cooling chamber of claim 1, comprising mounting means arranged on said insulating vessel for attaching working and observation apparatus thereto.

5. A cooling chamber for processing a specimen for microscopic and electron-microscopic investigations comprising:
    an insulating vessel having an inner wall surface defining a receiving cavity;
    coolant vessel means for holding a coolant therein and for defining a work chamber wherein the specimen is processed, said coolant vessel means being disposed in said cavity and having an outer wall surface adjacent said inner wall surface;
    a plurality of spacers arranged at preselected locations between said wall surfaces for supporting said coolant vessel means in spaced relationship to said inner wall surface thereby causing said wall surfaces to conjointly define an intermediate space therebetween;
    coolant supply means for supplying vaporized coolant to said work chamber;
    said coolant vessel means including: a coolant vessel having a base and a wall extending upwardly from said base to define a space for holding said coolant therein:
    a wall portion of said wall of said coolant vessel extending upwardly beyond the level of said coolant to define a portion of said work chamber;
    an ancillary wall section mounted on said coolant vessel, said ancillary wall section and said wall portion conjointly defining said work chamber; and,
    said work chamber including a base wall having a plurality of apertures formed therein so as to permit said vaporized coolant to pass into and fill said work chamber.

6. The cooling chamber of claim 5, said plurality of apertures being uniformly distributed over said base wall.

7. The cooling chamber of claim 6, said supply means comprising heating means for heating said coolant so as to increase the vaporization thereof.

8. The cooling chamber of claim 7, said heating means being disposed in said coolant vessel so as to be distributed at least approximately uniformly beneath said base wall of said work chamber.

9. A cooling chamber for processing a specimen for microscopic and electron-microscopic investigations comprising:

an insulating vessel having an inner wall surface defining a receiving cavity;

coolant vessel means for holding a coolant therein and for defining a work chamber wherein the specimen is processed, said coolant vessel means being disposed in said cavity and having an outer wall surface adjacent said inner wall surface;

a plurality of spacers arranged at preselected locations between said wall surfaces for supporting said coolant vessel means in spaced relationship to said inner wall surface thereby causing said wall surfaces to conjointly define an intermediate space therebetween;

coolant supply means for supplying vaporized coolant to said work chamber;

displaceable cover means made of heat-insulating material and being displaceable between a first position whereat said work chamber is closed off with respect to the ambient and a second position whereat said work chamber is open and accessible from the ambient; and, heating means for heating said coolant so as to increase the vaporization thereof, said heating means including a heater and a switch for switching said heater on and off, said switch being mounted relative to said cover means so as to be actuated for switching on said heater when said cover is moved into said second position.

10. A cooling chamber for processing a specimen for microscopic and electron-microscopic investigations comprising:

an insulating vessel having an inner wall surface defining a receiving cavity;

a coolant vessel for holding a coolant therein disposed in said cavity and having an outer wall surface adjacent said inner wall surface;

a wall extending upwardly from said coolant vessel to define an enclosure for processing the specimen, said wall extending upwardly short of said cover so as to cause the top edge of said wall and said cover to conjointly define a gap therebetween;

said enclosure having a base wall defining an interface between said enclosure and the interior of said coolant vessel, said base wall having aperture means formed therein so as to permit vaporous coolant to pass from said coolant vessel into said enclosure thereby filling the latter and then passing through said gap;

a plurality of spacers arranged at preselected locations between said wall surfaces for supporting said coolant vessel means in spaced relationship to said inner wall surface thereby causing said wall surfaces to conjointly define an intermediate space therebetween which communicates with said gap to receive vaporous coolant from said enclosure; and, coolant supply means for supplying vaporized coolant to said work chamber.

* * * * *

UNITED STATES PATENT AND TRADEMARK OFFICE
CERTIFICATE OF CORRECTION

PATENT NO. : 4,680,945

DATED : July 21, 1987

INVENTOR(S) : Dietrich Hoffmeister

It is certified that error appears in the above-identified patent and that said Letters Patent is hereby corrected as shown below:

In the Abstract, line 9: delete "is" and substitute -- so -- therefor.

In column 4, line 49: delete "therein:" and substitute -- therein; -- therefor.

In column 4, line 64: after the word "said", add the word -- coolant --.

Signed and Sealed this

Fifth Day of January, 1988

Attest:

DONALD J. QUIGG

*Attesting Officer*  *Commissioner of Patents and Trademarks*